United States Patent [19]

Mayer et al.

[11] Patent Number: 5,502,058

[45] Date of Patent: Mar. 26, 1996

[54] METHOD FOR THE TREATMENT OF PAIN

[75] Inventors: David J. Mayer; Donald D. Price; Jianren Mao, all of Richmond, Va.; John W. Lyle, Belmar, N.J.

[73] Assignee: Virginia Commonwealth University, Richmond, Va.

[21] Appl. No.: 246,184

[22] Filed: May 19, 1994

Related U.S. Application Data

[63] Continuation of Ser. No. 95,107, Jul. 21, 1993, which is a continuation-in-part of Ser. No. 27,177, Mar. 5, 1993, Pat. No. 5,352,683.

[51] Int. Cl.$^6$ .................................................. A61K 31/485
[52] U.S. Cl. ........................... 514/289; 514/626; 514/886
[58] Field of Search ..................................... 514/289, 886, 514/626

[56] References Cited

U.S. PATENT DOCUMENTS

| | | | |
|---|---|---|---|
| 4,316,888 | 2/1982 | Nelson | 434/127 |
| 4,446,140 | 5/1984 | Nelson | 424/260 |
| 4,994,467 | 2/1991 | Zimmerman | 514/284 |
| 5,164,398 | 11/1992 | Sims et al. | 514/282 |
| 5,352,683 | 10/1994 | Mayer et al. | 514/289 |

FOREIGN PATENT DOCUMENTS 0270290  6/1988  European Pat. Off. .

OTHER PUBLICATIONS

Rote Liste. Bundesverband Der Pharmazeutischen Industrie E.V., Editio Cantor, Aulendorf, 1992, Mando–Gripp.
Rote Liste. Bundesverband Der Pharmazeutischen Industrie E.V., Editio Cantor, Aulendorf, 1992, Husten–Und Fieber––Saft Ratiopharm/Husten–Under Fieber–Tabletten–Ratiopharm.
Rote Liste. Bundesverband Der Pharmazeutischen Industrie E.V., Edito Cantor, Aulendorf, 1992, Wick Formel 44 plus Husten–Pastillen.
Pharmacotherapy, vol. 10, No. 4, 1990, pp. 262–270.
Search Report from European Appln. No. 94103212.0 dated Jul. 26, 1994.
Brain Res., vol. 605, No. 1, 5 Mar. 1993, pp. 164–168.
Neurosci. Lett., vol. 151, No. 1, 5 Mar. 1993, pp. 107–110.
Eur. J. Pharmacol., vol. 212, No. 1, 1992, pp. 21–29.
Pain, vol. 51, No. 2, 1992, pp. 249–253.
Mao et al., "Intrathecal MK–801 and local nerve anesthesia synergistically reduce nociceptive behaviors in rats with experimental peripheral mononeuropathy", *Brain Research*, 576 (1992) 254–262 (Mao et al. I listed in the original Information Disclosure Statement).
Mao et al., "Post–injury treatment with GM1 ganglioside reduces nociceptive behaviors and spinal cord metabolic activity in rats with experimental peripheral mononeuropathy":, *Brain Research*, 584 (1992) 18–27 (Mao et al. II listed in the accompanying Second Supplemental Information Disclosure Statement).
Mao et al., "Intrathecal GM1 ganglioside and local nerve anesthesia reduce nociceptive behaviors in rats with experimental peripheral mononeuropathy", *Brain Research*, 584 (1992) 28–35 (Mao et al. III, listed in the accompanying Second Supplemental Information Disclosure Statement).
Mao et al., "Pain–related increases in spinal cord membrane–bound protein kinase C following peripheral nerve injury", *Brain Research*, 588 (1992) (Mao et al. IV listed in the Supplemental Information Disclosure Statement).
Neurosci. Lett., vol. 140, No. 2, 1992, pp. 181–184.

*Primary Examiner*—Shailendra Kumar
*Attorney, Agent, or Firm*—Dilworth & Barrese

[57] ABSTRACT

A method of alleviating pain such as neuropathic pain or acute inflammatory pain is provided which comprises administering to a mammal that is either exhibiting pain or is about to be subjected to a pain-causing event a pain alleviating/pain suppressing amount of at least one nontoxic antagonist for the N-methyl-D-aspartate receptor, e.g., dextrorphan, or metabolic precursor of such antagonist, e.g., dextromethorphan, or at least one nontoxic substance that blocks a major intracellular consequence of N-methyl-D-aspartate receptor activation, e.g., a phenothiazine such as trifluoperazine.

5 Claims, 4 Drawing Sheets

METHOD FOR THE TREATMENT OF PAIN

CROSS REFERENCE TO RELATED APPLICATION

This is a continuation of application Ser. No. 08/095,107 filed Jul. 21, 1993, which is a continuation-in-part of commonly assigned, U.S. patent application Ser. No. 08/027,177, filed Mar. 5, 1993, U.S. Pat. No. 5,352,683.

BACKGROUND OF THE INVENTION

This invention relates to methods for the treatment of pain and, in particular, to the alleviation of chronic pain and its varieties, e.g., neuropathic pain, and acute persistent pain that is related to inflammation of injured body tissues.

Chronic pain is persistent pain which has long outlasted the onset of any known or suspected physical cause. It can occur after a known injury or disease or it can occur without any known physical cause whatsoever. Moreover, it can be accompanied by known tissue pathology, such as chronic inflammation that occurs in some types of arthritis, or it can occur long after the healing of the injured tissue which is suspected or known to be the cause of chronic pain. Chronic pain is a very general concept and there are several varieties of chronic pain related to the musculoskeletal system, visceral organs, skin, and nervous system.

Neuropathic pain can occur as a form of chronic pain and can also occur under acute conditions such as those following surgery or accidental trauma. Neuropathic pain call be defined as pain that results from an abnormal functioning of the peripheral and/or central nervous system. A critical component of this abnormal functioning is an exaggerated response of pain-related nerve cells either in the peripheral or in the central nervous system. This exaggerated responsiveness is manifested behaviorally as increased sensitivity to pain, i.e., as hyperalgesia or allodynia, both of which can occur in chronic neuropathic and acute inflammatory pains. An example is the pain from causalgia wherein even a light touch to the skin is felt as an excruciating burning pain (allodynia) or a normally mild pain is experienced as an excruciating one (hyperalgesia).

Neuropathic pain is thought to be a consequence of damage to peripheral nerves or to regions of the central nervous system. However, abnormal functioning of pain-related regions of the nervous system call also occur with chronic inflammatory conditions such as certain types of arthritis and metabolic disorders such as diabetes as well as with acute inflammatory conditions. Thus, many types of chronic pains that are related to inflammation as well as acute pains that are related to inflammation can be considered to be at least partly neuropathic pains.

The long term administration of narcotic analgesics to patients suffering from various types of chronic pain, e.g., causalgia, hyperesthesia, sympathetic dystrophy, phantom limb syndrome, denervation, etc., is subject to a number of serious drawbacks including the development of opiate tolerance and/or dependence, severe constipation, and so forth.

U.S. Pat. No. 4,769,372 describes a method for treating chronic pain or chronic cough in a patient while preventing or alleviating the development of constipation or other symptoms of intestinal hypomotility wherein an opioid analgesic or antitussive such as morphine, meperidine, oxycodone, hydromorphone, codeine and hydrocodone is administered to the patient together with an opioid antagonist such as naloxone, naloxone glucuronide and nalmefene glucuronide. However successful this therapeutic combination may be in inhibiting the development of constipation or other symptoms of intestinal hypomotility, it does not address the problems of tolerance and/or dependence that are associated with the long term administration of narcotic analgesics.

Other approaches to the treatment of chronic pain/neuropathic pain have included the administration of a pharmaceutically acceptable acid addition salt or a protonated derivative of at least one microtubule inhibitor such as vinblastine, dexacetoxyvinblastine, vincristine, vindesine, leurosine and N-formyl-leurosine as disclosed in U.S. Pat. No. 4,602,909, (3S,4S)-7-hydroxy-$\Delta^6$-tetrahydrocannabinol homologues and derivatives essentially free of the (3R,4R) form as disclosed in U.S. Pat. No. 4,876,276, ganglioside $GM_1$ as disclosed in Hayes et al., *Pain*, 48(1992)391–396, Mao et al., *Brain Res.*, 584(1992)18–27, 584(1992)28–35 and 588(1992)144–149 and the N-methyl-D-aspartate (NMDA) receptor antagonist, or blocker, MK801 (the compound 5-methyl-10,11-dihydro-SH-dibenzo[a,d]cyclohepten-5,10-imine) and IIA966 (1-hydroxy-3 -aminopyridi-done-2) as disclosed in Mao et al., *Brain Res.*, 576(1992)254–262 and *Brain Res.*, 598 (1992) 271–278. It may be noted that MK 801 is unsuitable for use as a therapeutic due to its pronounced central nervous system neurotoxicity.

Dextrorphan, the main metabolite of the anticonvulsant dextromethorphan, and ketamine are known N-methyl-D-aspartate (NMDA) receptor antagonists but unlike MK 801, have few, if any, neurotoxic side effects. Heretofore there has been no recognition or appreciation that a nontoxic NMDA receptor antagonist would have any beneficial application to the treatment of pain or any of its varieties as well as acute pains that are likely to involve hyperalgesia/allodynia. Surprisingly, it has now been found that a non-toxic NMDA receptor antagonist such as dextrorphan exhibits significant ameliorating effects on certain types of chronic pain that result from nerve injury.

SUMMARY OF THE INVENTION

In accordance with the present invention, there is provided a method for the treatment of pain which comprises administering to a mammal that is either exhibiting pain or is about to be subjected to a pain-causing event a pain-alleviating amount of at least one nontoxic substance that blocks the NMDA receptor and/or that blocks a major intracellular consequence of NMDA receptor activation.

The method of this invention can be applied to the treatment of chronic (neuropathic) pain as well as the acute inflammatory pains that can occur after trauma to body tissues, e.g., those resulting from surgery, injuries, etc.

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan, or the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established criteria, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 whose toxicities effectively preclude their therapeutic use.

The term "pain-alleviating" shall be understood herein to include the expressions "pain-suppressing" and "pain-inhibiting" as the invention is applicable to the alleviation of existing pain as well as the suppression or inhibition of pain which would otherwise ensue from a pain-causing event.

DESCRIPTION OF THE PREFERRED EMBODIMENTS

Figure 1:
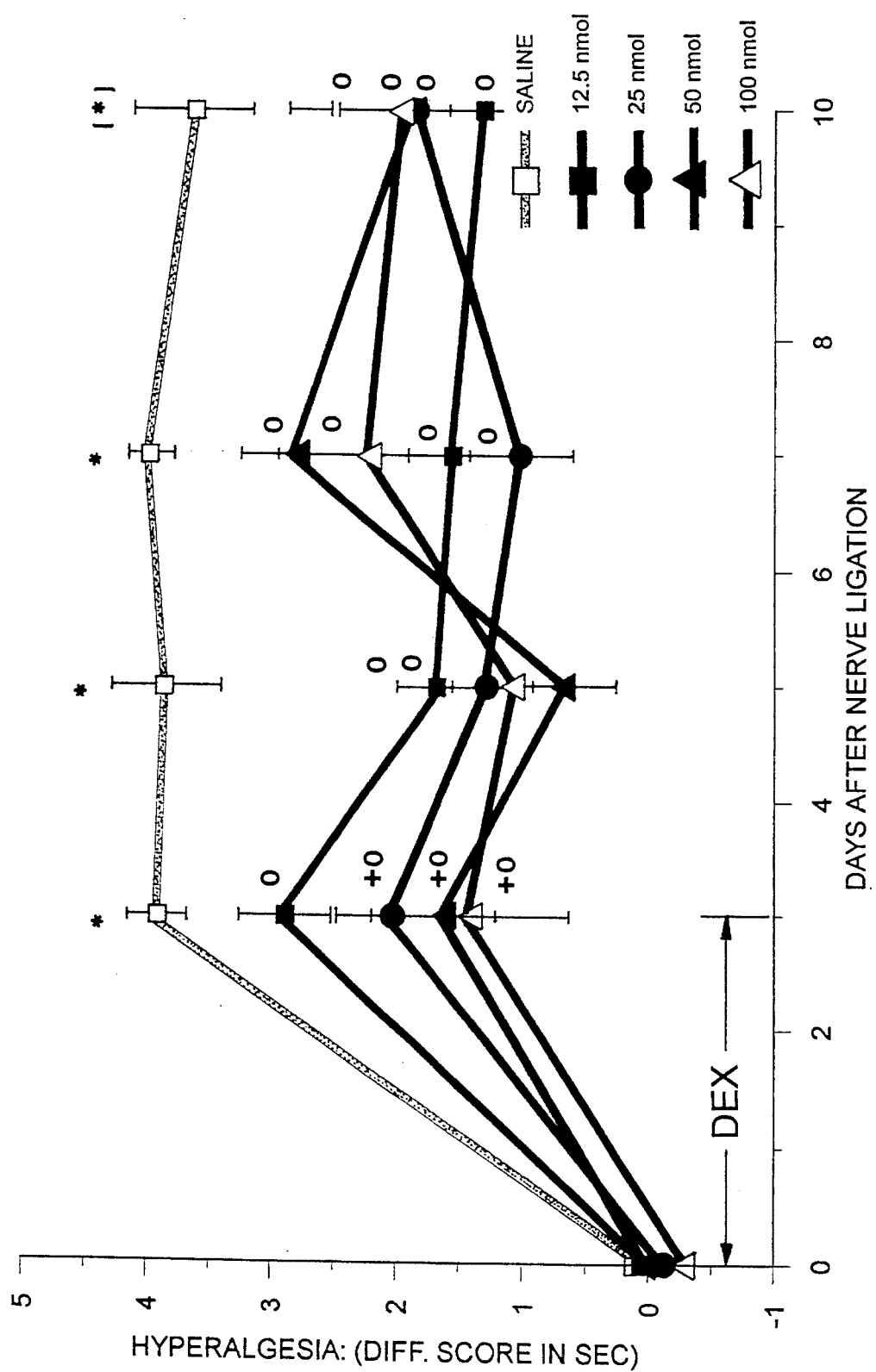
FIG. 1 is a graphical presentation of test results showing the therapeutic effects of intrathecal administration of dextrorphan on hyperalgesia in CCI (chronic constrictive injury) rats.

Among the nontoxic substances that block the NMDA receptor and as such are useful in the practice of the present invention are morphinans such as dextrorphan ((+)-3-hydroxy-N-methylmorphinan), dextromethorphan ((+)-3-hydroxy-N-methylmorphinan) which metabolizes to dextrorphan in the liver, their mixtures and the pharmaceutically acceptable salts thereof. Other useful nontoxic substances that block the NMDA receptor include ketamine (2-(2-chlorophenyl)-2-(methylamino)cyclohexanone), pyrroloquinoline quinone and cis-4-(phosphonomethyl)-2-piperidinecarboxylic acid.

As previously indicated, it is also within the scope of the invention to treat pain in a subject by administering to the subject at least one nontoxic substance that blocks a major intracellular consequence of NMDA receptor activation. Activation of the NMDA receptor, a subtype of excitatory amino acid receptors, induces a number of changes in the functional activity of nerve cells, and in particular, their capacity for excitability or inhibition in the presence of an addictive substance, via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→ autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/ or nucleic acid modification via scavenge of free radicals; iv) induction of neurotoxicity at higher nitric oxide levels; v) retrograde actions in adjacent neurons or glial cells such as facilitation of glutamate release/ NMDA receptor activation and/or inhibition of postsynaptic NMDA receptors→changes in functional activity;

e) interactions with the cyclic adenosine monophosphate/ protein kinase A system, the phospholipase C-inositol triphosphate-Ca++/diacylglycerol-protein kinase system, the phospholipase A2-arachidonic acid/prostanoids/leukotrienes system→changes in functional activity induced by second messenger systems other than NMDA receptor/$Ca^{++}$/$Ca^{++}$-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to treat pain by administering a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention.

Nontoxic substances that block a major intracellular consequence of NMDA receptor activation and are therefore useful in the practice of the invention include inhibitors of protein kinase C, e.g., amphipathic long chain bases such as sphingosine, N,N,N-trimethylsphingosine, sphinganine and psychosine; quinolyloxazole-2-ones such as 4-methyl-5-(3-quinolinyl)-2-(3H)-oxazolone and phenyl-5-(2-quinolinyl)-2-3(3H)-oxazolone; 1,4-bis-(amino-hydroxyalkylamino)-anthraquinones such as 1,4-bis-(3-propylamino-2-hydroxypropylamino)-9,10anthracenedione and 1,4-bis-(3-benzylamino-2 -hydroxypropylamino)-9,10 anthracenedione; and, mixtures and pharmaceutically acceptable salts of any of the foregoing.

Additional nontoxic substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1]benzoxazepines such as 1,3-dihydro-1-(1[(4-methyl-4H,6H-pyrrolo[1,2-a][4,1]benzoxazepin-4-yl)methyl]-4-piperidinyl)-2H-benzimidazol-2-one; benzhydryls such as N-[2](diphenylmethylthioethyl]-2-(trifluoromethyl)benzeneethanamine, N-[2-(bis(4-fluorophenyl)methylthio)ethyl] -2-(trifluoromethyl)benzeneethanamine and N-[2-(bis(4-fluorophenyl)methylthio)ethyl]-3-(trifluoromethyl)benzeneethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Administration of the nontoxic NMDA receptor antagonist and/or substance that blocks a major intracellular consequence of NMDA receptor activation ("pain-alleviating substance") can be by way of oral administration or by intravenous, intramuscular, subcutaneous, intrathecal, epidural or intracerebroventricular injection. The pain-alleviating substance can be administered to the patient just before the patient is about to be subjected or exposed to a pain-causing event such as surgery (i.e., as preemptive analgesia), or while the patient is experiencing pain. Effective dosage levels can vary widely, e.g., from about 0.25 to about 250 mg/day, but actual amounts will, of course, depend on the state and circumstances of the patient being treated. As those skilled in the art recognize, many factors that modify the action of the pain alleviating agent herein will be taken into account by the treating physician such as the age, body weight, sex, diet and condition of the patient, the time of administration, the rate and route of administration, and so forth. Optimal dosages for a given set of conditions can be ascertained by those skilled in the art using conventional dosage determination tests in view of the experimental data provided herein.

The pain-alleviating substance will ordinarily be formulated with one or more pharmaceutically acceptable ingredients in accordance with known and established practice. Thus, the pain alleviating substance can be formulated as a liquid, powder, elixir, injectable solution, etc. Formulations for oral use can be provided as hard gelatin capsules wherein the pain alleviating substance is mixed with an inert solid diluent such as calcium carbonate, calcium phosphate or kaolin, or as soft gelatin capsules wherein the pain alleviating substance is mixed with an oleaginous medium, e.g., liquid paraffin or olive oil.

Aqueous suspensions can contain the pain alleviating substance in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g., heptadecaethyleneoxycetanol, or condensation products of ethylene oxide with partial esters derived from fatty acids and a hexitol, e.g., polyoxyethylene sorbitol monooleate or condensation products of ethylene oxide with partial esters derived from fatty acids and hexitol anhydrides, e.g., polyoxyethylene sorbitan monooleate. Such aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide the pain-alleviating substance in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

The pain-alleviating substance is advantageously provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

It is also within the scope of this invention to treat pain by administration of the pain alleviating substance herein to the patient prior to, with or following the administration of indicated dosage levels of a local anesthetic such as bupivicaine hydrochloride, chloroprocaine hydrochloride, dibucaine, dibucaine hydrochloride, etidocaine hydrochloride, lidocaine, lidocaine hydrochloride, mepivacaine hydrochloride, piperocaine hydrochloride, prilocaine hydrochloride, procaine hydrochloride, propoxycaine hydrochloride tetracaine, tetracaine hydrochloride, and the like, and/or a nonsteroidal anti-inflammatory drug such as diflusenal, ibuprofen, indomethacin, meclofenamate sodium, mefenamic acid, naproxen, naproxen sodium, oxyphenbutazone, phenylbutazone, piroxicam, sulindac, tolmetin sodium, and the like. The local anesthetics will generally be applied directly or close to the nerve that is injured.

The examples that follow are illustrative of the invention. The animal model used in the experiments described below is that of neuropathic pain. Since the symptoms studied were manifested and measured during the first 10 days after the original sciatic nerve constriction injury, these studies apply to an acute pain condition, an early stage of neuropathic pain. However, since very similar symptoms occur in humans months and years after the original injury, these findings are likely to apply to chronic pain conditions as well.

EXAMPLES 1–3

These examples demonstrate the effectiveness of dextrorphan (Example 1) and ketamine (Example 2) in preventing the development of nociceptive behaviors (hyperalgesia and spontaneous pain-related behaviors) in rats with peripheral mononeuropathy induced by loose ligation of the common sciatic nerve, i.e., chronic constrictive injury (CCI), employing procedures for sciatic nerve ligation described in Bennett et al., Pain, 33 (1988)87–107 and in Mao et al., *Brain Res.*, 576(1992)254–262.

Adult male Sprague-Dawley rats (Hilltop) weighing 400–500 g at the time of surgery were used in these examples. Animals were individually housed in stainless steel cages under a 12 h light cycle (lights on from 0.700 to 19.00 h). Food and laboratory chow were available ad libitum. Animals were implanted with intrathecal (IT) catheters and their right common sciatic nerve was ligated under sodium pentobarbital (50 mg/kg, intraperitoneally) anesthesia. For IT catheter implantation, a segment of polyethylene tubing (PE 10) flushed with 0.4% gentamicin solution was inserted through a small incision at the atlanto-occipital membrane and gently advanced 8.5 cm caudally to the lumbosacral enlargement. The catheter was secured to a skull screw with dental acrylic cement and the rostral end was sealed with putty. For nerve ligation, the right common sciatic nerve was exposed at a level proximal to the sciatic trifurcation and separated from the connective tissue. The nerve was then loosely tied with four chromic gut (4-0) ligatures. The skin incision was closed with a 4-0 silk suture. All CCI rats were injected post-operatively with potassium penicillin (30,000 IU/rat) intramuscularly to prevent infection.

Hyperalgesia to radiant heat was assessed in the CCI rats employing the procedure described in Mao et al., *Brain Res.*, 584(1992)28–35 and 576(1992)254–262.

Pain threshold was determined by measuring the foot-withdrawal latency defined as the time from the onset of radiant heat to foot withdrawal. The baseline latency was adjusted to 10–11 s and the cut-off time was preset to 15 s in order to prevent tissue damage. Three test trials were made for each of the rat's hind paws. The mean withdrawal latency (MWL) of three test trials was used to calculate foot-withdrawal latency difference scores (MWL of non-ligated hind paw minus MWL of ligated hind paw). Spontaneous nociceptive behaviors were quantified for each CCI rat by using a spontaneous pain behavior rating method as described in Mao et al., *Brain Res.*, 584(1992)28–35 and 576(1992)254–262. Each rat was allowed to freely move within an open top transparent plastic cylinder (diameter 19 cm×height 30 cm) and, following an adaptation period of 5 min, the combined duration of two behaviors was recorded over three consecutive 5-min observation periods: (1) the placement of only the medial edge or the heel of the ligated hind paw on the ground, and (b) the lifting of that hind paw. For statistical evaluation, the average score of each animal over the three observation periods was used.

Dextrorphan (12.5, 25, 50 or 100 nmol in 10 μl), ketamine at equivolume and equimolar doses, or equivolume saline vehicle were administered IT at 24-h intervals for the first 4 consecutive days starting 1 h after surgery and ending 30 min prior to testing on day 3 post-surgery (n=6/group). Thermal hyperalgesia was assessed 1 day before surgery (baseline) and then on days 3, 5, 7 and 10 post-surgery. Intrathecal injection was given slowly over a 10- to 15-s period using a Hamilton 50-μl syringe and followed by 10 μl (void volume of catheters) of saline to flush the drug into the subarachnoid space.

Figure 2:
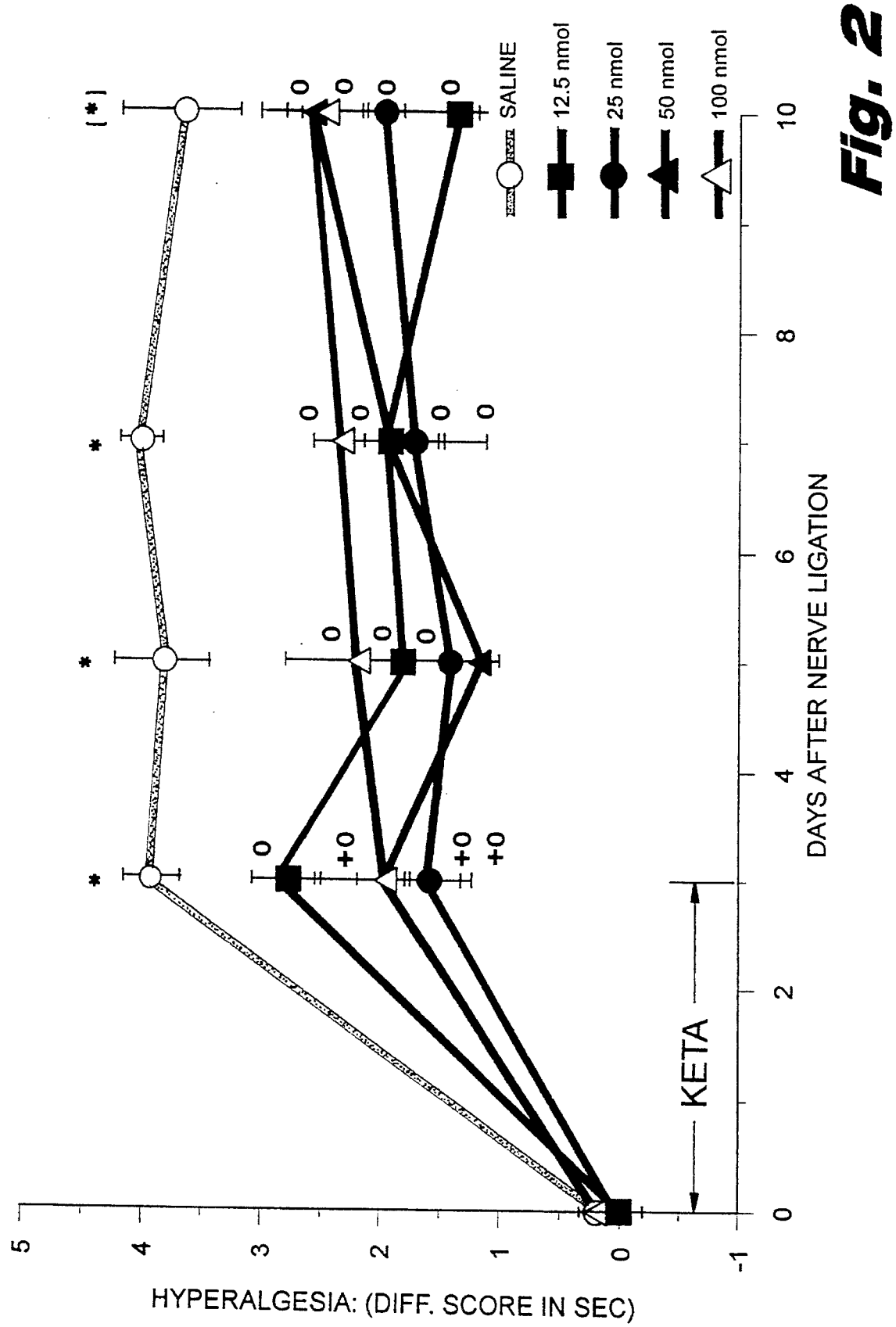
FIG. 2 is a graphical presentation of test results showing the therapeutic effects of intrathecal administration of ketamine on hyperalgesia in CCI rats.

The foot withdrawal latency difference scores for CCI rats treated with dextrorphan over the 10 day post-surgery evaluation period are set forth in FIG. 1 and the scores for the CCI rats treated with intrathecal ketamine are set forth in FIG. 2. The latency difference score shown on the y-axis was obtained by subtracting ipsilateral foot-withdrawal latencies from contralateral foot-withdrawal latencies, and standard errors are presented as vertical lines.

As indicated by these scores, foot withdrawal latency difference scores on day 3 after nerve ligation were reliably higher (3–4s) in CCI rats receiving saline treatment compared to their baseline scores and remained higher for the entire 10 day post-surgery period. Multiple intrathecal treatments with either dextrorphan (FIG. 1) or ketamine (FIG. 2) reliably reduced foot-withdrawal latency difference scores as compared to those of saline-treated CCI rats on days 3, 5 and 7 but, apart from the 12.5-nmol dose groups, not on day 10 post-surgery. This reduction of thermal hyperalgesia continued even after the withdrawal of dextrorphan prior to day 4 following nerve ligation. The foot withdrawal latency difference between two hind paws of CCI rats was due to a reduction of foot-withdrawal latency in the ligated hind paw, since the withdrawal latency of the non-ligated hind paw was unchanged as compared to baseline latencies, indicating the presence of thermal hyperalgesia in CCI rats. The lack of reliable reduction of thermal hyperalgesia in the remaining drug treatment groups on day 10 post-surgery may be due to the small sample size (n=6) of each group. The reduction of thermal hyperalgesia was partially dose related for both compounds on day 3 post-surgery (dextrorphan and ketamine; 100=50=25 nmol>12.5 nmol) but not on the remaining test days (FIGS. 1 and 2).

Figure 3:
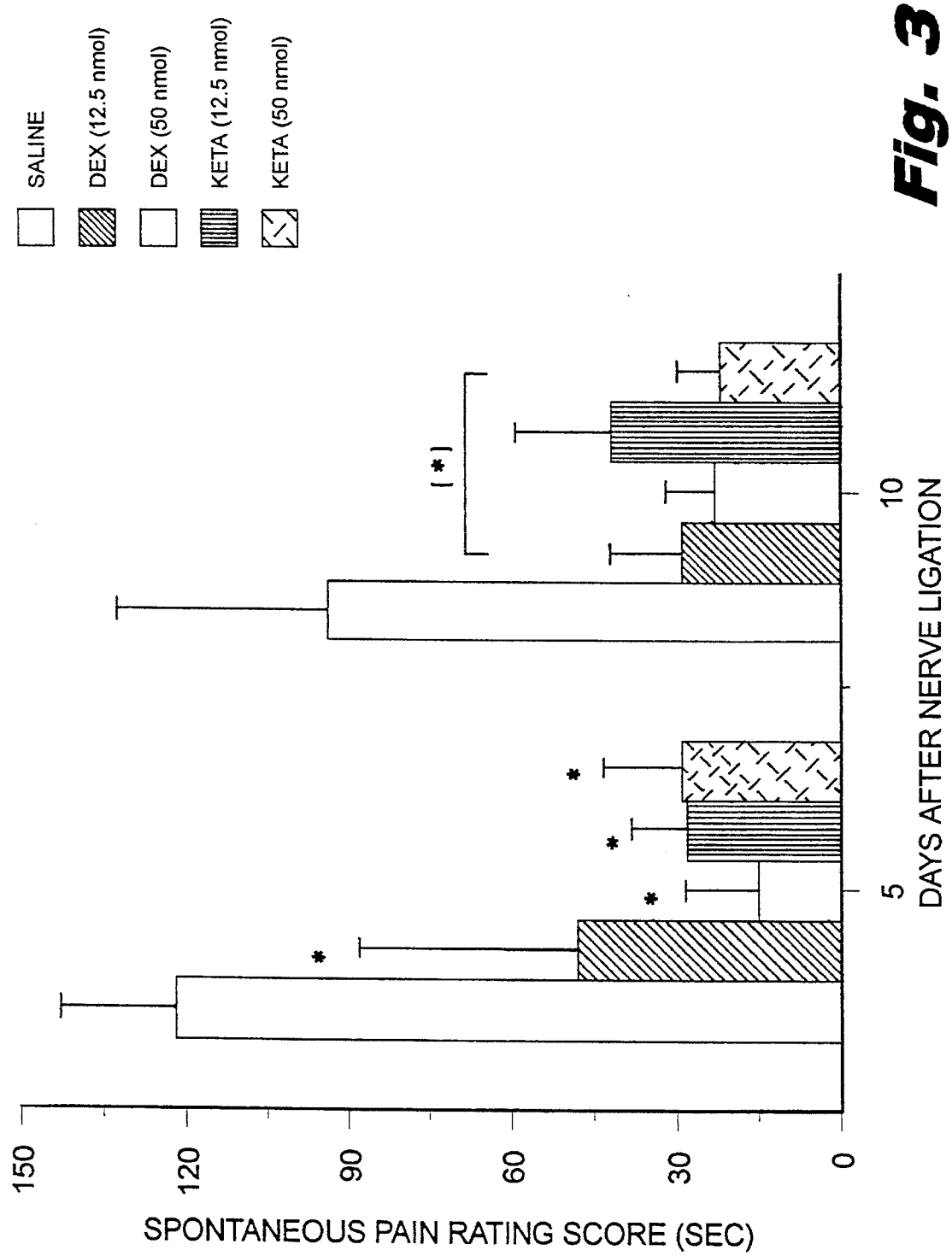
FIG. 3 is a graphical presentation of test results demonstrating attenuation of spontaneous pain-related behaviors in CCI rats treated with dextrorphan or ketamine; and, FIG. 4 is a graphical presentation of test results showing the therapeutic effects of dextrorphan or ketamine, given 3 days after nerve injury, on nociceptive behaviors in CCI rats.

Consistent with their effects on thermal hyperalgesia, multiple treatments with dextrorphan or ketamine (12.5, 50 nmol for each compound) also reduced spontaneous pain-rating scores in CCI rats on day 5 following nerve ligation (FIG. 3) indicating the attenuation of spontaneous pain-related behaviors. Spontaneous pain-rating scores on day 10 post-surgery were, however, not significantly different between the saline group and each of drug treatment groups. This was likely due to the small sample size (n=7/group) since spontaneous pain-rating scores were reliably higher in the saline group as compared to the treatment group pooled from four drug treatment groups.

EXAMPLE 4

This example demonstrates the therapeutic effectiveness of dextrorphan and ketamine on nociceptive behaviors in CCI rats. Unlike examples 1–3 which illustrate prevention, these effects represent the reversal of pain-related behaviors caused by constrictive injury of the sciatic nerve.

Figure 4:
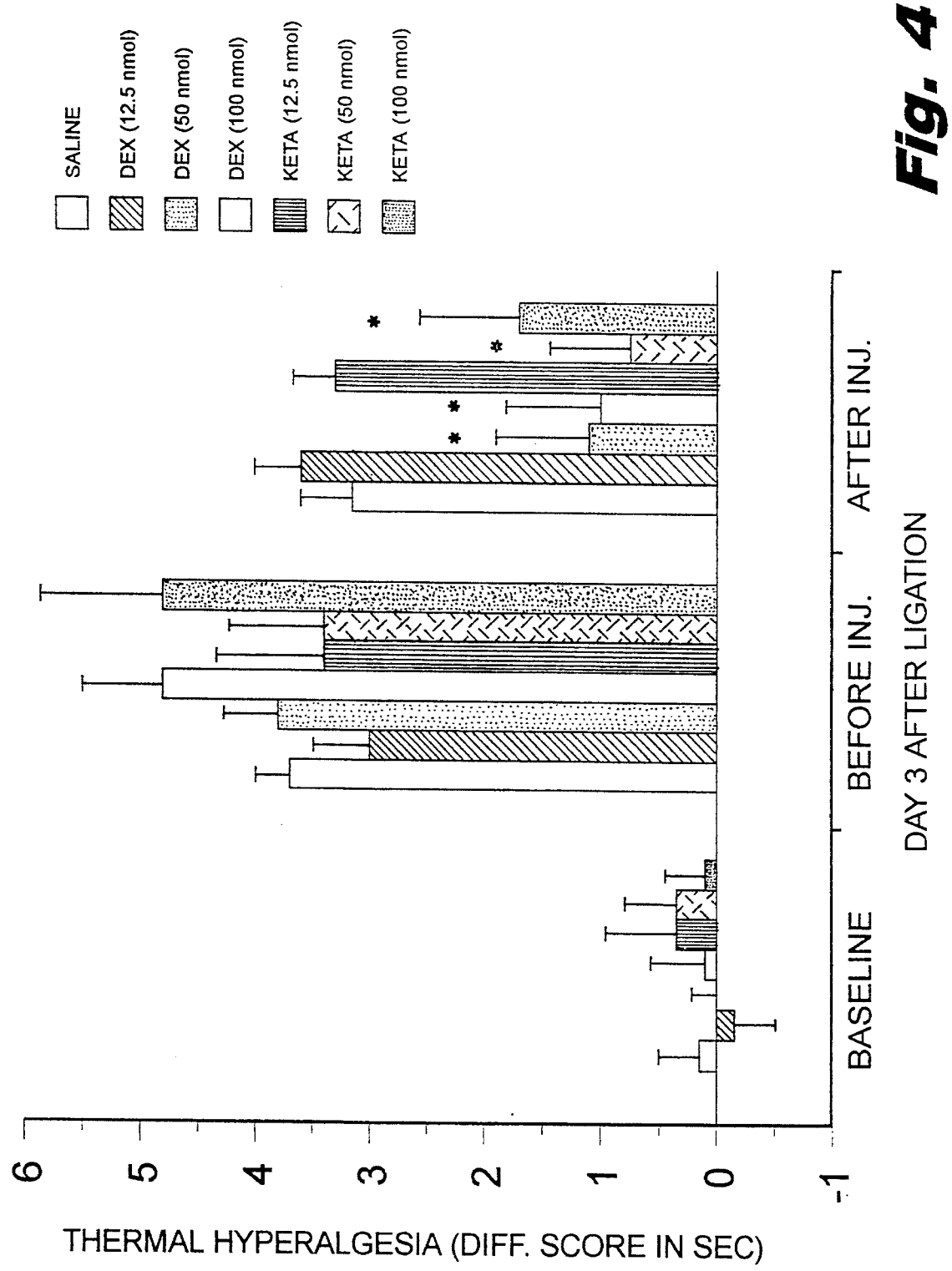

Seven groups (n=7/group) of CCI rats received a single IT treatment with either dextrorphan or ketamine (12.5, 50, and 100 nmol for each compound) or IT saline injection on day 3 after nerve ligation. As shown in FIG. 4, the CCI rats in all 7 groups exhibited thermal hyperalgesia before treatment on day 3 post-surgery as demonstrated by reliably higher foot-withdrawal latency difference scores as compared to baseline latency difference scores. Thirty minutes after each treatment, foot-withdrawal latency difference scores were reliably lower in CCI rats treated with 50 or 100 nmol (but not 12.5 nmol) dextrorphan or ketamine as compared to those receiving a single saline treatment. The reduction of thermal hyperalgesia was nearly complete since latency difference scores in CCI rats treated with dextrorphan or ketamine (50 or 100 nmol) were not significantly different from their baseline scores indicating a potent reduction of thermal hyperalgesia in these CCI rats by an acute, single treatment with dextrorphan or ketamine.

What is claimed is:

1. A method of alleviating pain which comprises administering to a mammal that is either exhibiting pain or is about to be subjected to a pain-causing event a pain-alleviating amount of (a) at least one member selected from the group consisting of dextromethorphan, dextrorphan, their mixtures and their pharmaceutically acceptable salts and (b) lidocaine or pharmaceutically acceptable salt thereof with (a) being administered prior to, with or following the administration of (b).

2. The method of claim 1 wherein the pain is chronic pain or acute inflammatory pain.

3. A therapeutic composition comprising (a) at least one member selected from the group consisting of dextromethorphan, dextrorphan, their mixtures and their pharmaceutically acceptable salts and (b) lidocaine or pharmaceutically acceptable salt thereof.

4. The method of claim 1 wherein the pain is neurophathic pain.

5. The method of claim 1 wherein (a) and (b) are administered prior to surgery.

* * * * *